(12) United States Patent
Wang et al.

(10) Patent No.: US 9,074,109 B2
(45) Date of Patent: Jul. 7, 2015

(54) FLUORINE-CONTAINING POLYMER, THE PREPARATION PROCESS AND USE THEREOF, PIGMENT DISPERSION AND THE PREPARATION PROCESS

(71) Applicant: BOE Technology Group Co., LTD., Beijing (CN)

(72) Inventors: Xuelan Wang, Beijing (CN); Zhuo Zhang, Beijing (CN); Jisheng Zhao, Beijing (CN); Chen Liu, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 124 days.

(21) Appl. No.: 14/082,949

(22) Filed: Nov. 18, 2013

(65) Prior Publication Data
US 2014/0142220 A1    May 22, 2014

(30) Foreign Application Priority Data
Nov. 19, 2012   (CN) .......................... 2012 1 0468331

(51) Int. Cl.
| | | |
|---|---|---|
| C09D 163/00 | (2006.01) | |
| C09D 161/04 | (2006.01) | |
| C08K 5/103 | (2006.01) | |
| C08K 5/11 | (2006.01) | |
| C08K 5/12 | (2006.01) | |
| C07C 67/00 | (2006.01) | |
| C07C 67/14 | (2006.01) | |
| C07C 69/003 | (2006.01) | |
| C07C 69/28 | (2006.01) | |
| C07C 69/62 | (2006.01) | |
| C07C 69/76 | (2006.01) | |
| C08G 63/682 | (2006.01) | |

(52) U.S. Cl.
CPC ............ *C09D 163/00* (2013.01); *C08G 63/682* (2013.01); *C09D 161/04* (2013.01); *C08K 5/103* (2013.01); *C08K 5/11* (2013.01); *C08K 5/12* (2013.01); *C07C 67/00* (2013.01); *C07C 67/14* (2013.01); *C07C 69/003* (2013.01); *C07C 69/28* (2013.01); *C07C 69/62* (2013.01); *C07C 69/76* (2013.01)

(58) Field of Classification Search
None
See application file for complete search history.

(56) References Cited

U.S. PATENT DOCUMENTS 4,487,823 A * 12/1984 Lehmann et al. ............... 430/56

FOREIGN PATENT DOCUMENTS

| | | |
|---|---|---|
| CN | 101506257 A | 8/2009 |
| CN | 102015904 A | 4/2011 |
| CN | 102453354 A | 5/2012 |
| JP | 2009-29979 A | 2/2009 |

OTHER PUBLICATIONS

Zhuang et al. "Rheological Properties of Semidilute Solutions of Poly(acrylic acid) Modified with Hydrocarbon and Fluorocarbon End-Capped Poly(ethylene glycol) Macromonomer"; 2002.*
First Office Action (including English translation) for Chinese patent application No. 2012104683319, dated Apr. 8, 2014, 15 pages.
Liu, Guo-qiang et al., "Preparation and characterization of a kind of non-ionic fluorocarbon surfactants", Fine and Specialty Chemicals, Jan. 2011, 4 pages (English translation of Abstract only).

* cited by examiner

*Primary Examiner* — Michael J Feely
(74) *Attorney, Agent, or Firm* — Westman, Champlin & Koehler, P.A.

(57) ABSTRACT

The present invention relates to a fluorine-containing polymer comprising a structure represented by the following general formula (I), as well as the preparation process and use thereof. According to the technical solution of the invention, a novel fluorine-containing polymer with a larger molecular weight and an aromatic side group is obtained through a simple reaction, and it can be used as a non-ionic fluorine carbon surfactant, and especially, is applicable to the preparation of a pigment dispersion. Additionally, the invention further relates to a pigment dispersion and the preparation process thereof. In the invention, a little non-ionic fluorine carbon surfactant is added into a traditional pigment dispersion, whereby the interface energy in the pigment dispersion system can be improved, and the aggregation and agglomeration of pigment particles are prevented, as a result, the particle diameter and viscosity are less changed with the lapse of time, and there is no precipitate occurred, therefore, the stability of the pigment dispersion is improved significantly.

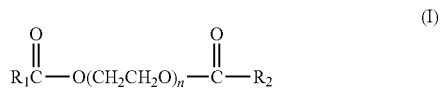

(I)

16 Claims, 10 Drawing Sheets

FLUORINE-CONTAINING POLYMER, THE PREPARATION PROCESS AND USE THEREOF, PIGMENT DISPERSION AND THE PREPARATION PROCESS

CROSS-REFERENCE TO RELATED APPLICATION

This application is a non-provisional Application of Chinese Application No. CN 201210468331.9, filed Nov. 19, 2012 in Chinese, the contents of which are hereby incorporated by reference in their entirety.

FIELD OF THE INVENTION

The invention relates to the field of polymeric surfactants and the field of pigment dispersions, and specifically, relates to a novel fluorine-containing polymer, the preparation process and use thereof, and further relates to a pigment dispersion added with a non-ionic fluorine carbon surfactant and the preparation process thereof.

BACKGROUND OF THE INVENTION

At present, the traditionally used main manufacturing process for producing a color film layer on a color filter is the pigment dispersing process, whose basic principle includes the steps of coating a pigment light-blocking agent onto a transparent substrate, and then irritating the same with a ray such as the ray from an ultraviolet lamp so as to cure the pigment light-blocking agent and form the color film layer. The pigment light-blocking agent comprises a pigment dispersion, a monomer, an oligomer, a diluent, a leveling agent and a solvent or the like, and the pigment dispersion mainly comprises a colored pigment, a dispersant, a resin and a solvent. The stability of the pigment dispersion is very important. If there are precipitates produced in the pigment dispersion, the pigment light-blocking agent prepared by using this pigment dispersion will also produce precipitates, which will cause directly the surface of the color film layer on the color filter uneven, apt to produce mura, and thus, the qualified ratio of the product will be decreased. If there is the phenomenon of agglomeration in the pigment dispersion, such pigment dispersion cannot be used for formulating the pigment light-blocking agent.

Pigment powders are generally consisted of 0.02-0.5 μm fine crystal grains. There is a strong trend of aggregation and agglomeration among the crystal grains due to the small particle diameter, large specific surface area and high interface energy of the crystal grains. In order to qualify the contrast degree of a color filter, the particle diameter of the pigment in a pigment light-blocking agent is generally required to be tens of nanometers. Thus, in the preparation process of a pigment dispersion, the surface of the pigment should be further treated so as to make it stable in a range of tens of nanometers. In order to prevent the agglomeration of pigment particles, for example, the pigment is subjected to an inorganic acid treatment, a mechanical graining process, or a treatment in which an additive such as a dispersant, a resin and a low molecular compound of a pigment derivative or the like is added. Still, there have been not reported a process for effectively improving the stability of a pigment dispersion at present.

SUMMARY OF THE INVENTION

In the prior art, there have been not reported a process for effectively improving the stability of a pigment dispersion, as well as an additive particularly applicable to a pigment dispersion. In order to overcome this technical defect and find a novel surfactant, the object of the invention is to provide a fluorine-containing polymer which can be used as a fluorine carbon surfactant.

Another object of the invention is to provide a process for preparing the fluorine-containing polymer.

Another object of the invention is to provide a use of the fluorine-containing polymer.

Another object of the invention is to provide a pigment dispersion whose stability is improved significantly.

Another object of the invention is to provide a process for preparing the pigment dispersion.

The fluorine-containing polymer provided in the invention has a structure represented by a general formula (I):

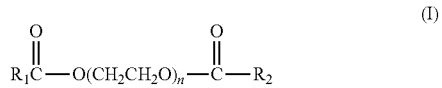

wherein, $R_1$ is a C1-C10 perfluoroalkyl; $R_2$ is a substituted or unsubstituted group selected from a phenyl group, a benzyl group, a benzo-heterocyclic group or a naphthyl group; and n=3-35.

The lower limit of n is preferably 4, more preferably 5, and the upper limit thereof is preferably 30, more preferably 15.

Wherein, in the substituted $R_2$ group, the substituent is a C1-C5 alkyl group, a C2-C5 alkenyl group, a C1-C5 alkoxy group, a C2-C5 acyl group, or a halogen atom.

Preferably, $R_1$ is a C1-C5 perfluoroalkyl group; and $R_2$ is a phenyl group, a benzodihydropyranyl group or a naphthyl group.

More preferably, the fluorine-containing polymer has the structure represented by one of the following formulae:

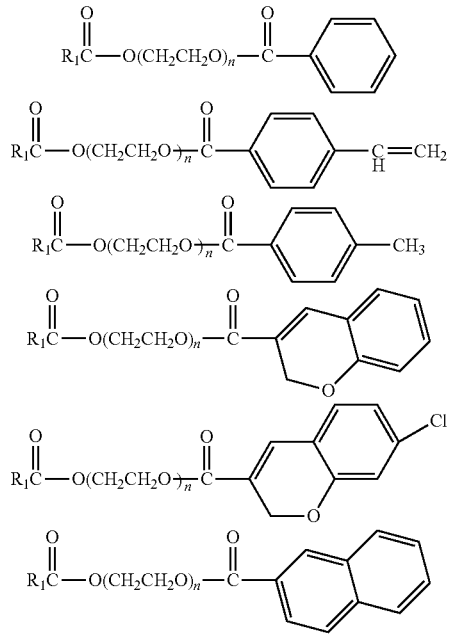

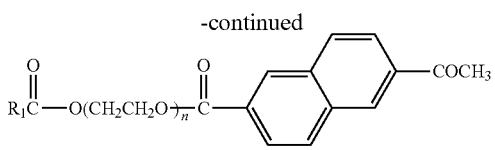

The invention provides a process for preparing the fluorine-containing polymer, comprising the steps of:

(1) preparing a perfluoroalkyl carboxylic acid having the following formula:

$R_1COOH$, wherein $R_1$ is a C1-C10 perfluoroalkyl group;

(2) subjecting the perfluoroalkyl carboxylic acid obtained in step (1) and a polyethylene glycol to an esterification reaction to obtain a polyethylene glycol monoester product;

(3) subjecting the esterification product obtained in step (2) and a carboxylic acid $R_2$—COOH to an esterification reaction to obtain the fluorine-containing polymer.

Wherein, $R_2$ is a substituted or unsubstituted group selected from phenyl group, benzyl group, a benzo-heterocyclic group or naphthyl group.

In the above preparation process, the perfluoroalkyl carboxylic acid in step (1) is preferably obtained from a perfluoroalkyl acyl halide as a starting material through esterification and hydrolysis, and wherein the perfluoroalkyl acyl halide is preferably a perfluoroalkyl acyl fluoride or a perfluoroalkyl acyl chloride.

In the above preparation process, the polyethylene glycol in step (2) is preferably $HO(CH_2CH_2O)_nH$, wherein n=3-35.

In the esterification reaction of step (2), an acidic catalyst such as concentrated sulfuric acid, p-toluene sulfonic acid or the like, a traditional organic solvent such as a benzene type solvent, and a traditional operation such as water separation by reflowing or the like used for the traditional esterification reactions can be used. The specific process conditions can be determined by those skilled in the art.

The first use of the fluorine-containing polymer provided in the invention is the use as a non-ionic fluorine carbon surfactant.

The second use of the fluorine-containing polymer provided in the invention is the use in a pigment dispersion.

The invention provides a pigment dispersion comprising a pigment, wherein the pigment dispersion further comprises a non-ionic fluorine carbon surfactant.

The weight of the non-ionic fluorine carbon surfactant is 1-15%, preferably, 3-10% of the weight of the pigment.

The non-ionic fluorine carbon surfactant can be an existing non-ionic fluorine carbon surfactant, such as FC4430, and can also be the fluorine-containing polymer represented by the general formula (I) in the invention. The non-ionic fluorine carbon surfactant can greatly decrease the surface tension in the pigment dispersion system so as to improve the stability of the pigment dispersion. Additionally, the fluorine-containing polymer represented by the general formula (I) comprises an aromatic side group introduced into the molecule chain thereof, which can increase the compatibility between the dispersant and the pigment so as to further improve the stability of the pigment dispersion.

Preferably, the invention further provides a pigment dispersion comprising a pigment, wherein the pigment dispersion further comprises a non-ionic fluorine carbon surfactant which is the fluorine-containing polymer represented by the general formula (I) according to any one of the above technical solutions.

The weight of the non-ionic fluorine carbon surfactant is 1-15%, preferably, 3-10% of the weight of the pigment.

The pigment dispersion provided in the invention comprises by weight the following ingredients of:

| | |
|---|---|
| pigment: | 1 part; |
| solvent: | 0.5-10 parts; |
| dispersant: | 0.05-1.0 parts; |
| resin: | 0.01-1.0 parts; |
| pigment intensifier: | 0.01-0.5 parts; |
| non-ionic fluorine carbon surfactant: | 0.01-0.15 parts. |

Preferably, the pigment dispersion comprises by weight the following ingredients of:

| | |
|---|---|
| pigment: | 1 part; |
| solvent: | 1-5 parts; |
| dispersant: | 0.1-0.8 parts; |
| resin: | 0.05-0.5 parts; |
| pigment intensifier: | 0.01-0.1 parts; |
| non-ionic fluorine carbon surfactant: | 0.03-0.1 parts. |

In the pigment dispersion, the components other than the non-ionic fluorine carbon surfactant can be selected from any components used in the existing pigment dispersions.

Preferably, the pigment is selected from the traditional colored materials.

The solvent is selected from propylene glycol methyl ether acetate, propylene glycol diacetate, or ethyl 3-ethoxylpropionate.

The dispersant is a solvent type wetting dispersant, and preferably, and preferably a commercially available superdispersant, such as BYK series (BYK Chemie, Germany) super-dispersants, solsperse series (Lubrizol Company, Germany) super-dispersants, or the similar super-dispersants made in China, or the like.

The resin is selected from an epoxy resin or a phenolic resin.

The pigment intensifier is selected from an azo type pigment intensifier, a phthalocyanin type pigment intensifier, or a quinacridone type pigment intensifier. The pigment intensifier (which is also referred to as a compatibilizer or a dispersion aid) comprises a pigment-philic group and thus, it can function between the pigment and the dispersant so as to make the dispersant to improve the de-flocculation and stability of the pigment more effectively. The selection of the pigment intensifier is related to the type of the pigment and should accommodate the type of the dispersant. Preferably, a commercially available pigment intensifier, such as BYK series (BYK Chemie, Germany) pigment intensifiers, solsperse series (Lubrizol Company, Germany) pigment intensifiers, or the similar pigment intensifiers made in China, or the like, can be utilized.

The invention provides a process for preparing the pigment dispersion comprising the steps of:

(1) a pre-dispersing step wherein a pigment mixture is obtained by mixing and stirring a solvent, a dispersant, a resin and a pigment intensifier uniformly, adding a pigment and a non-ionic fluorine carbon surfactant, and then stirring uniformly;

(2) a grinding step wherein the obtained pigment mixture is grained to obtain the pigment dispersion.

Preferably, the time of the grinding in step (2) is 1-10 hours.

The pre-dispersing step specifically comprises mixing a solvent, a dispersant, a resin and a pigment intensifier, stirring the obtained mixture at a rotating rate of 1500-6000 rpm for 30-60 min, then adding a pigment and a non-ionic fluorine carbon surfactant thereto, and stirring the obtained mixture at a rotating rate of 1500-6000 rpm for 40-90 min, so as to obtain a pigment mixture.

The grinding step specifically comprises subjecting the pigment mixture to grinding at a rotating rate of 300-800 rpm for 5-15 min, then at a rotating rate of 1000-4000 rpm for 1-6 hours, and finally, at a rotating rate of 300-800 rpm for 5-30 min, so as to obtain the pigment dispersion.

In the pigment dispersion obtained in the above preparation process, the particle diameters of the pigment particles are 40-60 nm According to the technical solution of the invention, a novel fluorine-containing polymer with a higher molecular weight and an aromatic side group is obtained through a simple chemical reaction, which can be used as a non-ionic fluorine carbon surfactant, and especially, is applicable to the preparation of a pigment dispersion, and can greatly improve the stability of the pigment dispersion system and prevent the pigment from agglomeration and precipitation.

In the technical solution of the invention, a small amount of non-ionic fluorine carbon surfactant is added into a traditional pigment dispersion, whereby the interface energy in the pigment dispersion system can be improved, and the aggregation and agglomeration of pigment particles are prevented, as a result, the particle diameter and viscosity of the pigment are less changed with the lapse of time, and there is no precipitate occurred, therefore, the stability of the pigment dispersion is improved significantly. The preparation process provided in the invention comprises adding a non-ionic fluorine carbon surfactant at a pre-dispersing stage, which is operated simply under mild conditions and has a prospect of large-scale application.

Figure 1:
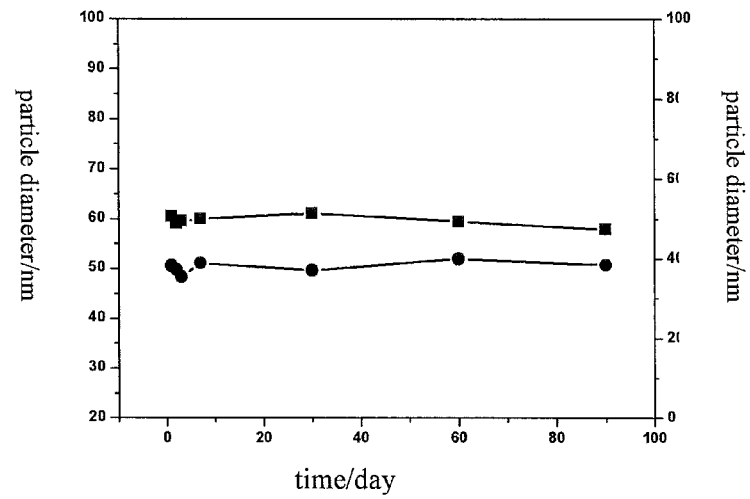
FIG. 1 is a chart showing the relation between the particle diameter of the pigment in the pigment dispersion of example 1 and the lapse of time.

In the above figures, the curve —●— represents the results of particle diameter or viscosity at 25° C., which is denoted by ordinate on the left; the curve —■— represents the results of particle diameter or viscosity at 41° C., which is denoted by ordinate on the right.

DETAILED DESCRIPTION OF THE INVENTION

The following examples are used for illustrating the invention, but not limiting the scope of the invention.

Preparation of Fluorine-Containing Polymer

The amounts of materials added in the following reactions are represented by molar parts, unless specified otherwise. For the contents not specified, such as the addition amount of a solvent, the addition amount of a catalyst or the like, they are deemed as the traditional operations in the field.

The reaction scheme is as follows:

$$R_1CF \xrightarrow{CH_3OH} R_1\overset{O}{\overset{\|}{C}}OCH_3 \longrightarrow R_1\overset{O}{\overset{\|}{C}}OH \xrightarrow{PEG}$$
$$\quad\quad\quad\quad\quad\quad 1 \quad\quad\quad\quad\quad 2$$

$$R_1\overset{O}{\overset{\|}{C}}-O(CH_2CH_2O)_nH \xrightarrow[R_2COOH]{H_2SO_4} R_1\overset{O}{\overset{\|}{C}}-O(CH_2CH_2O)_n-\overset{O}{\overset{\|}{C}}-R_2$$
$$\quad\quad\quad 3 \quad\quad\quad\quad\quad 4 \quad\quad\quad\quad\quad\quad\quad\quad\quad\quad I$$

In the above reaction scheme, $R_1$ is a C1-C10 perfluoroalkyl; $R_2$ is a substituted or unsubstituted group selected from a phenyl group, a benzyl group, a benzo-heterocyclic group or a naphthyl group; n is 3-35, preferably 4-30, and more preferably 5-15.

Wherein, in the substituted $R_2$ group, the substituent is a C1-C5 alkyl group, a C2-C5 alkenyl group, a C1-C5 alkoxy group or a halogen atom.

Preferably, $R_1$ is a C1-C5 perfluoroalkyl group; and $R_2$ is a phenyl group, a benzodihydropyranyl group or a naphthyl group.

The synthesis steps are as follows:

(1) Into a clean three-necked flask equipped with a thermometer, a condenser and a constant pressure dropping funnel, 5.2 parts of a perfluoroalkyl acyl fluoride $R_1COF$, 0.8 part of concentrated HCl are added in turn, and 5.8 parts of methanol is slowly added dropwise under magnetic stirring. After the addition, the mixture is allowed to react under reflow at about 120° C. overnight. The reaction is stopped and cooled to room temperature. The pH of the mixture is adjusted to about 7.0 with a 0.5 mol/L KOH solution. Layers are separated with a funnel, and the organic phase is extracted with methanol, washed with an aqueous saturated NaCl solution, and dried over anhydrous sodium sulfate to obtain a light yellow oil liquid, that is, the compound 1.

(2) 5 parts of the compound 1 is placed into a clean three-necked flask, and 12.3 parts of methanol and 51 parts of a KOH solution with a concentration of 4 mol/L are added thereto. The mixture is heated to 85° C. under magnetic stirring and refluxed for about 38 hrs, and then subjected to reduced pressure distillation so as to remove methanol. After cooling to room temperature, the solution is acidified by adding 1.2 mol/L hydrochloric acid solution and extracted with ethyl acetate. The organic phases are combined, washed with an aqueous saturated NaCl solution, dried over anhydrous sodium sulfate and filtered so as to obtain a white crystal, that is, the compound 2.

(3) Into a clean three-necked flask equipped with a thermometer, a condenser and a water segregator, 1.1 parts of the compound 2, 5 parts of polyethylene glycol (PEG) and xylene solvent are added in turn, and a catalytic amount of p-toluene sulfonic acid is added as a catalyst. The mixture is heated to 105° C. under magnetic stirring and reacted until there is no water produced in the water segregator. After the reaction, the xylene solvent is removed by reduced pressure distillation and the mixture is cooled to room temperature. The organic phase is washed with a saturated sodium carbonate solution to remove the un-reacted raw materials and the p-toluene sulfonic acid catalyst. Then, the product is dissolved in tetrahydrofuran, subjected to suction filtration to remove residual sodium carbonate. The product is subjected to reduced pressure distillation to remove tetrahydrofuran and vacuum dried to obtain the product 3.

(4) 1 part of the product 3 and 1.5 parts of the compound 4 are placed into a clean three-necked flask equipped with a thermometer, a condenser and a water segregator, xylene as a solvent and a catalytic amount of p-toluene sulfonic acid as a catalyst are added. The mixture is heated to about 105° C. under magnetic stirring and reacted until there is no water produced in the water segregator. After the reaction, the xylene solvent is removed by reduced pressure distillation and the mixture is cooled to room temperature. The organic phase is washed with a saturated sodium carbonate solution to remove the un-reacted raw materials and the p-toluene sulfonic acid catalyst. Then, the product is dissolved in tetrahydrofuran, subjected to suction filtration to remove the residual sodium carbonate. The resultant product is subjected to reduced pressure distillation to remove tetrahydrofuran and vacuum dried to obtain the product 5, that is, the fluorine-containing polymer as represented by general formula (I).

Preparation of Fluorine-Containing Polymer 1:

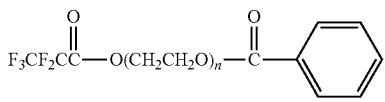

The fluorine-containing polymer 1 is prepared according to the above process, wherein the original reactant is perfluoroethyl acyl fluoride, the polyethylene glycol is PEG400, and the compound 4 is benzoic acid. In the obtained fluorine-containing polymer 1, $R_1$ is perfluoroethyl, $R_2$ is phenyl, and n is 8-11. The proton assignment and chemical shift values in Nuclear Magnetic Resonance Spectroscopy (CDCl$_3$, 300 MHz) are shown as follows.

| Proton Assignment | δ(ppm) |
|---|---|
| —O(CH$_2$CH$_2$O) | 3.45-3.95 |
| Ar-2,6-H | 8.07 |
| Ar-3,5-H | 7.58 |
| Ar-4-H | 7.66 |

Preparation of Fluorine-Containing Polymer 2:

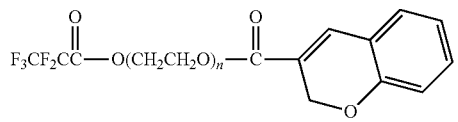

The fluorine-containing polymer 2 is prepared according to the above process, wherein the original reactant is perfluoroethyl acyl fluoride, the polyethylene glycol is PEG400, and the compound 4 is 2H-benzopyran-3-carboxylic acid. In the obtained fluorine-containing polymer 2, $R_1$ is perfluoroethyl, $R_2$ is benzodihydropyranyl, and n is 8-11. The proton assignment and chemical shift values in Nuclear Magnetic Resonance Spectroscopy (CDCl$_3$, 300 MHz) are shown as follows.

| Proton Assignment | δ(ppm) |
|---|---|
| —O(CH$_2$CH$_2$O) | 3.56-4.01 |
| Ar-8-H | 6.83 |
| Ar-7-H | 7.01 |
| Ar-6-H | 6.96 |
| Ar-5-H | 7.74 |
| Ar-4-H | 8.76 |
| CH$_2$—O | 4.54 |

Preparation of Fluorine-Containing Polymer 3:

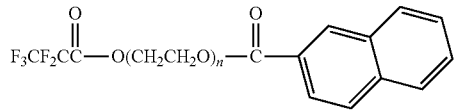

The fluorine-containing polymer 3 is prepared according to the above process, wherein the original reactant is perfluoroethyl acyl fluoride, the polyethylene glycol is PEG400, and the compound 4 is 2-naphthalenecarboxylic acid. In the obtained fluorine-containing polymer 3, $R_1$ is perfluoroethyl, $R_2$ is 2-naphthyl, and n is 8-11. The proton assignment and chemical shift values in Nuclear Magnetic Resonance Spectroscopy (CDCl$_3$, 300 MHz) are shown as follows.

| Proton Assignment | δ(ppm) |
|---|---|
| —O(CH$_2$CH$_2$O) | 3.47-3.98 |
| Ar-1-H | 10.11 |
| Ar-3-H | 7.88 |
| Ar-4-H | 7.42 |
| Ar-5-H | 7.95 |
| Ar-6-H | 7.63 |
| Ar-7-H | 7.71 |
| Ar-8-H | 8.34 |

Preparation of Fluorine-Containing Polymer 4:

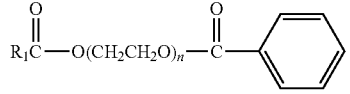

The fluorine-containing polymer 4 is prepared according to the above process, wherein the original reactant is perfluoroethyl acyl fluoride, the polyethylene glycol is PEG200, and the compound 4 is benzoic acid. In the obtained fluorine-containing polymer 4, $R_1$ is perfluoroethyl, $R_2$ is phenyl group, and n is 4-6. The proton assignment and chemical shift values in Nuclear Magnetic Resonance Spectroscopy (CDCl$_3$, 300 MHz) are shown as follows.

| Proton Assignment | δ(ppm) |
|---|---|
| —O(CH$_2$CH$_2$O) | 3.47-3.98 |
| Ar-2,6-H | 8.09 |
| Ar-3,5-H | 7.56 |
| Ar-4-H | 7.64 |

Preparation of Fluorine-Containing Polymer 5:

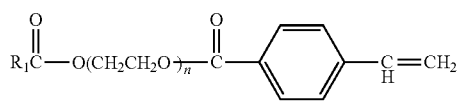

The fluorine-containing polymer 5 is prepared according to the above process, wherein the original reactant is perfluoroethyl acyl fluoride, the polyethylene glycol is PEG400, and the compound 4 is p-vinyl benzoic acid. In the obtained fluorine-containing polymer 5, $R_1$ is perfluoroethyl, $R_2$ is p-vinyl phenyl, and n is 8-11. The proton assignment and chemical shift values in Nuclear Magnetic Resonance Spectroscopy (CDCl$_3$, 300 MHz) are shown as follows.

| Proton Assignment | δ(ppm) |
|---|---|
| —O(CH$_2$CH$_2$O), | 3.45-4.05 |
| —CH=CH$_2$ | 5.53, 4.82 |
| Ar—2,6-H | 8.12 |
| Ar—3,5-H | 7.52 |

Preparation of Fluorine-Containing Polymer 6:

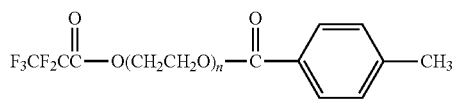

The fluorine-containing polymer 6 is prepared according to the above process, wherein the original reactant is perfluoroethyl acyl fluoride, the polyethylene glycol is PEG600, and the compound 4 is p-methyl benzoic acid. In the obtained fluorine-containing polymer 6, $R_1$ is perfluoroethyl, $R_2$ is p-methyl phenyl, and n is 13-15. The proton assignment and chemical shift values in Nuclear Magnetic Resonance Spectroscopy (CDCl$_3$, 300 MHz) are shown as follows.

| Proton Assignment | δ(ppm) |
|---|---|
| Ar—CH$_3$ | 2.33 |
| —O(CH$_2$CH$_2$O) | 3.49-3.99 |
| Ar-2,6-H | 8.10 |
| Ar-3,5-H | 7.55 |

Preparation of Fluorine-Containing Polymer 7:

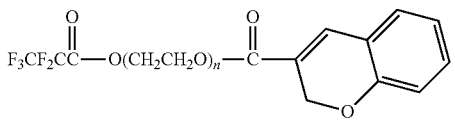

The fluorine-containing polymer 7 is prepared according to the above process, wherein the original reactant is perfluoroethyl acyl fluoride, the polyethylene glycol is PEG1000, and the compound 4 is 2H-benzopyran-3-carboxylic acid. In the obtained fluorine-containing polymer 7, $R_1$ is perfluoroethyl, $R_2$ is benzodihydropyranyl, and n is 20-23. The proton assignment and chemical shift values in Nuclear Magnetic Resonance Spectroscopy (CDCl$_3$, 300 MHz) are shown as follows.

| Proton Assignment | δ(ppm) |
|---|---|
| —O(CH$_2$CH$_2$O) | 3.54-4.03 |
| Ar-8-H | 6.85 |
| Ar-7-H | 7.03 |
| Ar-6-H | 6.94 |
| Ar-5-H | 7.75 |
| Ar-4-H | 8.74 |
| CH$_2$—O | 4.52 |

Preparation of Fluorine-Containing Polymer 8:

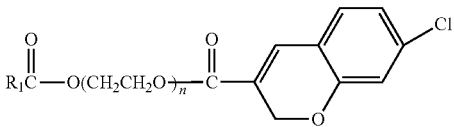

The fluorine-containing polymer 8 is prepared according to the above process, wherein the original reactant is perfluoroethyl acyl fluoride, the polyethylene glycol is PEG600, and the compound 4 is 2H-5-chloro-benzopyran-3-carboxylic acid. In the obtained fluorine-containing polymer 8, $R_1$ is perfluoroethyl, $R_2$ is 5-chloro-benzodihydropyranyl, and n is 13-15. The proton assignment and chemical shift values in Nuclear Magnetic Resonance Spectroscopy (CDCl$_3$, 300 MHz) are shown as follows.

| Proton Assignment | δ(ppm) |
|---|---|
| —O(CH$_2$CH$_2$O) | 3.58-4.07 |
| Ar-8-H | 6.89 |
| Ar-6-H | 6.73 |
| Ar-4-H | 8.79 |
| CH$_2$—O | 4.58 |

Preparation of Fluorine-Containing Polymer 9:

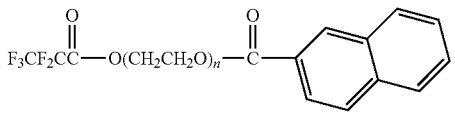

The fluorine-containing polymer 9 is prepared according to the above process, wherein the original reactant is perfluoroethyl acyl fluoride, the polyethylene glycol is PEG1500, and the compound 4 is 2-naphthalenecarboxylic acid. In the obtained fluorine-containing polymer 9, $R_1$ is perfluoroethyl, $R_2$ is 2-naphthyl, and n is 25-30. The proton assignment and chemical shift values in Nuclear Magnetic Resonance Spectroscopy (CDCl$_3$, 300 MHz) are shown as follows.

| Proton Assignment | δ(ppm) |
|---|---|
| —O(CH$_2$CH$_2$O) | 3.48-4.03 |
| Ar-1-H | 10.09 |
| Ar-3-H | 7.91 |
| Ar-4-H | 7.45 |
| Ar-5-H | 7.92 |
| Ar-6-H | 7.64 |
| Ar-7-H | 7.73 |
| Ar-8-H | 8.38 |

Preparation of Fluorine-Containing Polymer 10:

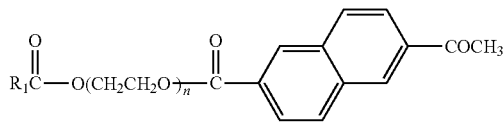

The fluorine-containing polymer 10 is prepared according to the above process, wherein the original reactant is perfluoroethyl acyl fluoride, the polyethylene glycol is PEG600, and the compound 4 is 6-acetyl-2-naphthalenecarboxylic acid. In the obtained fluorine-containing polymer 10, $R_1$ is perfluoroethyl, $R_2$ is 6-acetyl-2-naphthyl, and n is 13-15. The proton assignment and chemical shift values in Nuclear Magnetic Resonance Spectroscopy (CDCl$_3$, 300 MHz) are shown as follows.

| Proton Assignment | δ(ppm) |
|---|---|
| —O(CH$_2$CH$_2$O) | 3.47-3.98 |
| —COCH$_3$ | 3.82 |
| Ar-1-H | 10.13 |
| Ar-3-H | 7.91 |
| Ar-4-H | 7.38 |
| Ar-5-H | 7.97 |
| Ar-7-H | 7.68 |
| Ar-8-H | 8.37 |

EXAMPLE 1

Pigment Dispersion Comprising FC4430 Surfactant (1) Pre-Dispersion of Raw Materials Into a clean feed cylinder, 3 parts by weight of propylene glycol methyl ether acetate solvent was added, and then 0.5 part by weight of solsperse 24000 dispersant, 0.2 part by weight of a A81 resin (Laropal A 81, Guangzhou Jinhong Chemical Co., Ltd), 0.05 part by weight of a solsperse 12000 pigment intensifier were added into the feed cylinder in turn. The mixture was stirred under a rotating rate of 3000 rpm for about 40 min. Then, the obtained mixture was added with 1 part of G58 pigment (DIC Company) (CAS Number: 728018-63-1) and 0.05 part by weight of FC4430 fluorine carbon surfactant (3M Company), and stirred under a rotating rate of 3000 rpm for about 30 min to obtain a pigment mixture.

(2) Grinding

The pigment mixture obtained in the pre-dispersion stage was loaded into a sand mill, grinded under a rotating rate of 500 rpm for 10 min firstly, then grinded under a rotating rate of 2000 rpm for about 5 hours; after that, the mixture was further grained under a reduced rotating rate of 400 rpm for about 15 min. After the sand grinding, the obtained pigment dispersion was discharged from the sand mill.

The changes of the viscosity and particle diameter of the pigment particles in the pigment dispersion with the lapse of time were checked, and the bottom of the container was observed visually to see whether there was any precipitate produced. The method for this evaluation comprised observing the changes of the viscosity and particle diameter with the lapse of time at normal temperature (25° C.) and at 41° C. The evaluating results for the pigment dispersion in example 1 were shown in Table 1.

TABLE 1

The changes of particle diameter and viscosity of pigment particles in the pigment dispersion of example 1 with the lapse of time

| Time (day) | 1 | 2 | 3 | 7 | 30 | 60 | 90 |
|---|---|---|---|---|---|---|---|
| Particle diameter (nm) (25° C.) | 50.61 | 49.78 | 48.38 | 51.12 | 49.66 | 52.01 | 50.75 |
| Particle diameter (nm) (41° C.) | 50.63 | 48.92 | 49.36 | 48.98 | 51.33 | 49.35 | 47.33 |
| Viscosity (cps) (25° C.) | 4.82 | 4.88 | 4.83 | 4.82 | 4.85 | 4.82 | 4.84 |
| Viscosity (cps) (41° C.) | 4.88 | 4.84 | 4.79 | 4.85 | 4.78 | 4.83 | 4.80 |
| State of precipitation | No | No | No | No | No | No | No |

Figure 2:
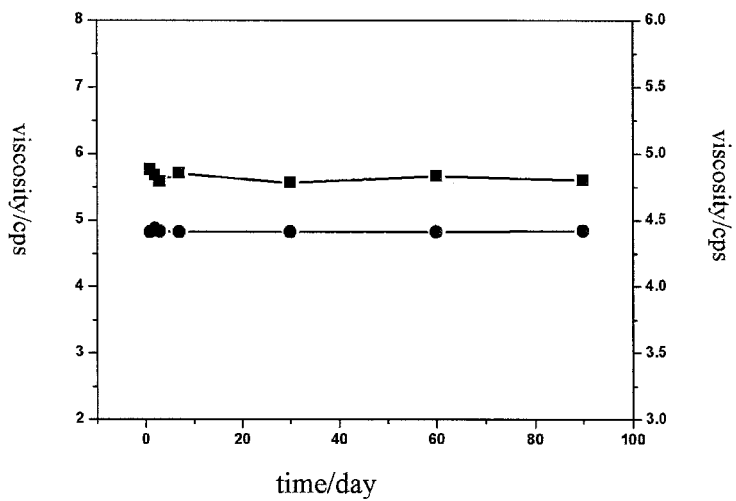
FIG. 2 is a chart showing the relation between the viscosity of the pigment in the pigment dispersion of example 1 and the lapse of time.

The relation between the changes of the viscosity and particle diameter of the pigment particles in the above pigment dispersion and the lapse of time were shown in FIGS. 1 and 2. From the results in Table 1 and FIGS. 1 and 2, it can be seen that when FC4430 fluorine carbon surfactant was added during the pre-dispersion stage, the changes of the viscosity and particle diameter of the obtained pigment particles were all very small, and there was no precipitate produced, and thus, the stability of the pigment dispersion was improved significantly.

COMPARATIVE EXAMPLE 1

The steps in example 1 were repeated expect that the surfactant FC4430 was not added. The evaluating results for the pigment dispersion obtained in comparative example 1 were shown in Table 2.

TABLE 2

The changes of particle diameter and viscosity of pigment particles in the pigment dispersion of comparative example 1 with the lapse of time

| Time (day) | 1 | 2 | 3 | 7 | 30 | 60 | 90 |
|---|---|---|---|---|---|---|---|
| Particle diameter (nm) (25° C.) | 49.63 | 87.34 | 88.62 | 100.41 | 206.56 | 208.97 | 220.35 |

TABLE 2-continued

The changes of particle diameter and viscosity of pigment particles in the pigment dispersion of comparative example 1 with the lapse of time

| Time (day) | 1 | 2 | 3 | 7 | 30 | 60 | 90 |
|---|---|---|---|---|---|---|---|
| Particle diameter (nm) (41° C.) | 48.56 | 82.48 | 86.56 | 104.25 | 210.37 | 212.31 | 233.26 |
| Viscosity (cps) (25° C.) | 4.80 | 7.82 | 18.35 | 30.58 | flocculation | flocculation | flocculation |
| Viscosity (cps) (41° C.) | 4.85 | 7.86 | 17.61 | 25.66 | flocculation | flocculation | flocculation |
| State of precipitation | No | A little sand like precipitate | A lot of sand like precipitate | A thick layer of precipitate on the bottom | A thick layer of precipitate on the bottom | A thick layer of precipitate on the bottom | A thick layer of precipitate on the bottom |

Figure 3:
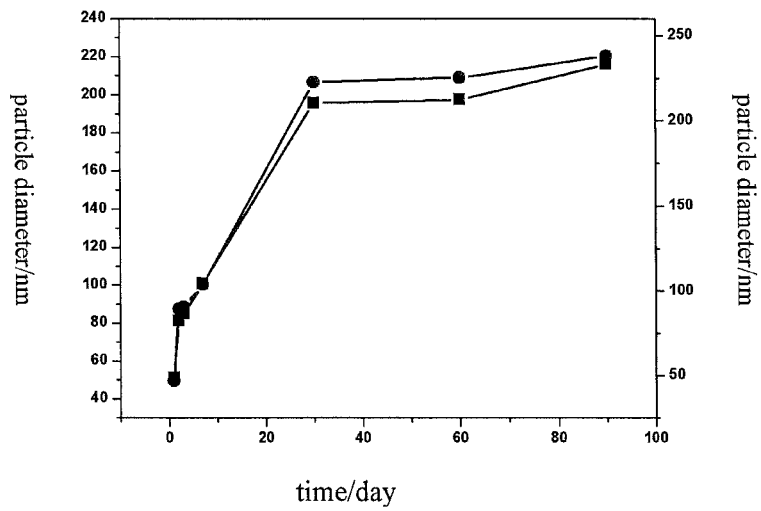
FIGS. 3-5 are charts showing the relation between the particle diameters of the pigments in the pigment dispersions of comparative examples 1-3 and the lapse of time, respectively.

The relation between the changes of the particle diameter of the pigment particles in the above pigment dispersion and the lapse of time was shown in FIG. 3. From the results in Table 2 and FIG. 3, it can be seen that when a surfactant was not added, the particle diameter in the pigment dispersion upon discharging could reach about 50 nm. However, after one day, the particle diameter increased quickly and reached 100 nm or more in one week. The viscosity also increased continuously and after one month, the pigment dispersion became a state of flocculation. The stability of the pigment dispersion was very poor.

COMPARATIVE EXAMPLE 2

The steps in example 1 were repeated expect that the surfactant FC4430 was not added during the pre-dispersion stage, instead, it was added about one hour after the beginning of the grinding step. The evaluating results for the pigment dispersion obtained in comparative example 1 were shown in Table 3.

TABLE 3

The changes of particle diameter and viscosity of pigment particles in the pigment dispersion of comparative example 2 with the lapse of time

| Time (day) | 1 | 2 | 3 | 7 | 30 | 60 | 90 |
|---|---|---|---|---|---|---|---|
| Particle diameter (nm) (25° C.) | 50.00 | 57.34 | 68.62 | 80.41 | 126.56 | 169.97 | 250.56 |
| Particle diameter (nm) (41° C.) | 50.04 | 52.48 | 66.56 | 84.25 | 110.37 | 158.33 | 243.32 |
| Viscosity (cps) (25° C.) | 4.78 | 6.82 | 15.35 | 25.43 | flocculation | flocculation | flocculation |
| Viscosity (cps) (41° C.) | 4.81 | 6.86 | 14.61 | 23.12 | flocculation | flocculation | flocculation |
| State of precipitation | No | A little sand like precipitate | A little sand like precipitate | A lot of sand like precipitate | A lot of sand like precipitate | A thick layer of precipitate on the bottom | A thick layer of precipitate on the bottom |

Figure 4:
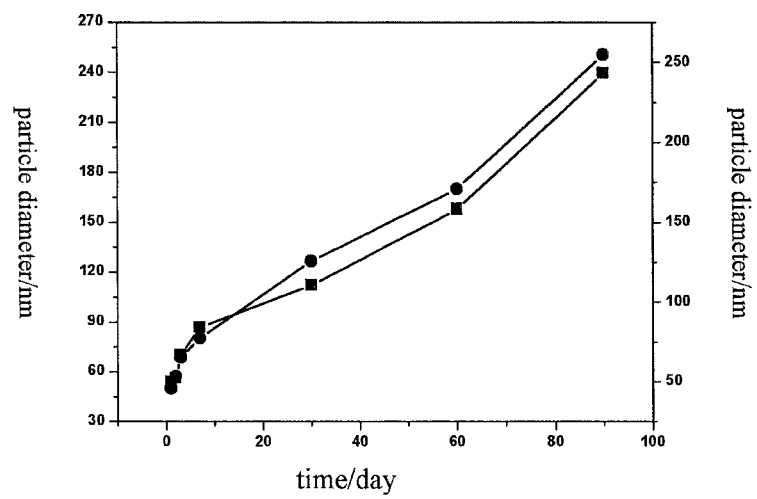

The relation between the changes of the particle diameter of the pigment particles in the above pigment dispersion and the lapse of time was shown in FIG. 4. From the results in Table 3 and FIG. 4, it can be seen that when the surfactant was added during the grinding stage, the change degree of the pigment particle diameter and viscosity with the lapse of time in one week became smaller, which was better than the case in comparative example 1 where FC4430 was not added. However, the changes increased continuously and more quickly with the lapse of time. In one week, a lot of precipitates occurred on the bottom of the container, and increased continuously. Thus, it can be seen that the stability of the pigment dispersion was inferior.

COMPARATIVE EXAMPLE 3

The steps in example 1 were repeated expect that the surfactant FC4430 was not added during the pre-dispersion stage and the grinding stage, instead, FC4430 was added alone after the grinding stage, and then the mixture was stirred at a rotating rate of about 500 rpm for about 10 min to mix it uniformly. The evaluating results for the pigment dispersion obtained in comparative example 3 were shown in Table 4.

TABLE 4

The changes of particle diameter and viscosity of pigment particles in the pigment dispersion of comparative example 3 with the lapse of time

| Time (day) | 1 | 2 | 3 | 7 | 30 | 60 | 90 |
|---|---|---|---|---|---|---|---|
| Particle diameter (nm) (25° C.) | 51.20 | 53.22 | 64.23 | 75.36 | 98.69 | 189.97 | 200.9 |
| Particle diameter (nm) (41° C.) | 49.69 | 51.33 | 61.56 | 68.33 | 95.87 | 178.66 | 196.45 |
| Viscosity (cps) (25° C.) | 4.83 | 7.55 | 12.33 | 28.56 | flocculation | flocculation | flocculation |
| Viscosity (cps) (41° C.) | 4.81 | 7.65 | 12.65 | 27.35 | flocculation | flocculation | flocculation |
| State of precipitation | No | A little sand like precipitate | A little sand like precipitate | A little precipitate | A little precipitate | A little precipitate | A little precipitate |

Figure 5:
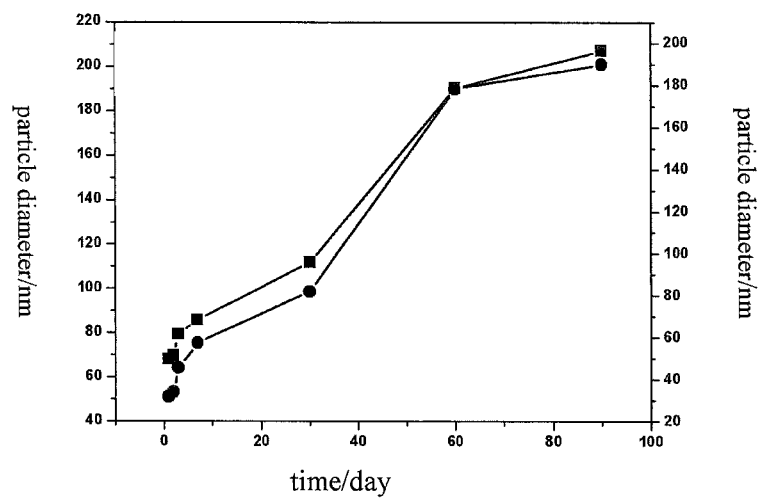

The relation between the changes of particle diameter of pigment particles in the above pigment dispersion and the lapse of time was shown in FIG. 5. From the results in Table 4 and FIG. 5, it can be seen that when the surfactant was added after the grinding stage, the change degree of the pigment particle diameter and viscosity in one week with the lapse of time became smaller, which was better than the case in comparative example 1 where FC4430 was not added. However, the changes of the pigment particle diameter and viscosity increased continuously and more quickly with the lapse of time. In one week, a little precipitate occurred on the bottom of the container, and it increased continuously, but the amount of the precipitate was obviously less than that in comparative example 1. Thus, it can be seen that the stability of the pigment dispersion was still inferior.

From the results of example 1 and comparative examples 1-3, it can be seen that when the surfactant FC4430 was added into the pigment dispersion, the effect of stabilization would be better than the case where FC4430 was not added. However, the addition timing of the surfactant had large influence on the effect of stabilization. When a certain amount of a fluorine-containing polymer was added during the pre-dispersion stage, the changes of the particle diameter and viscosity of pigment particles in the obtained pigment dispersion with the lapse of time became very small and there was no precipitate produced. Thus, the stability of the pigment dispersion was improved significantly.

EXAMPLE 2

Pigment Dispersion Comprising Fluorine-Containing Polymer 1

(1) Pre-Dispersion of Raw Materials

Into a clean feed cylinder, 4 parts by weight of propylene glycol diacetate solvent was added, and then 0.4 part by weight of BYK 21324 dispersant, 0.1 part by weight of A81 resin, 0.05 part by weight of BYK 2105 pigment intensifier were add into the feed cylinder in turn. The mixture was stirred under a rotating rate of 3000 rpm for about 40 min. Then, the obtained mixture was added with 1 part by weight of G58 pigment and 0.03 part of fluorine-containing polymer 1, and stirred under a rotating rate of 3000 rpm for about 30 min to obtain a pigment mixture.

(2) Grinding

The process in the grinding was the same as that in example 1.

The evaluating results (according to the same method as mentioned in example 1) for the pigment dispersion in example 2 were shown in Table 5.

TABLE 5

The changes of particle diameter and viscosity of pigment particles in the pigment dispersion of example 2 with the lapse of time

| Time (day) | 1 | 2 | 3 | 7 | 30 | 60 | 90 |
|---|---|---|---|---|---|---|---|
| Particle diameter (nm) (25° C.) | 47.83 | 47.35 | 48.95 | 48.66 | 46.27 | 48.23 | 48.59 |
| Particle diameter (nm) (41° C.) | 47.55 | 46.38 | 48.22 | 47.39 | 48.03 | 47.97 | 48.25 |
| Viscosity (cps) (25° C.) | 4.50 | 4.58 | 4.61 | 4.47 | 4.45 | 4.56 | 4.54 |
| Viscosity (cps) (41° C.) | 4.52 | 4.53 | 4.55 | 4.49 | 4.49 | 4.51 | 4.54 |
| State of precipitation | No | No | No | No | No | No | No |

Figure 6:
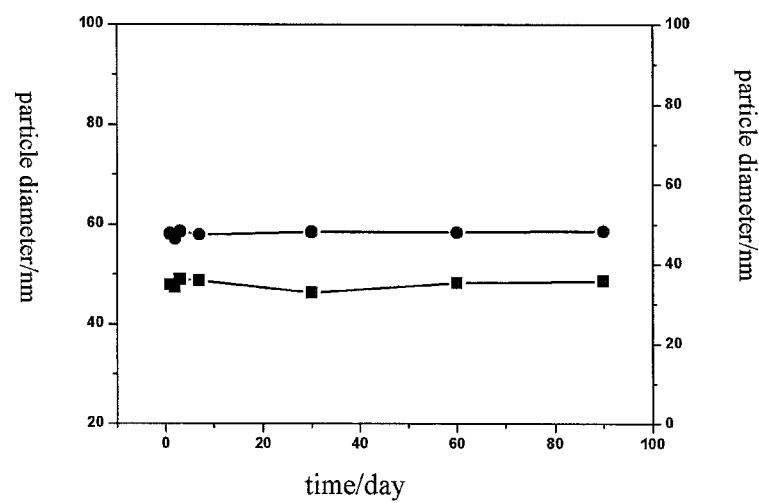
FIG. 6 is a chart showing the relation between the particle diameter of the pigment in the pigment dispersion of example 2 and the lapse of time.
Figure 7:
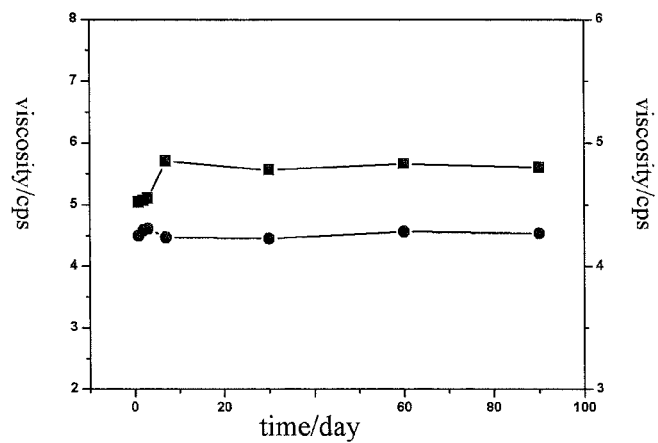
FIG. 7 is a chart showing the relation between the viscosity of the pigment in the pigment dispersion of example 2 and the lapse of time.

The relation between the changes of the viscosity and particle diameter of the pigment particles in the above pigment dispersion and the lapse of time were shown in FIGS. 6 and 7. From the results in Table 5 and FIGS. 6 and 7, it can be seen that when fluorine-containing polymer 1 as a fluorine carbon surfactant was added during the pre-dispersion stage, the changes of the viscosity and particle diameter of the obtained pigment particles were all very small, and there was no precipitate produced, and thus, the stability of the pigment dispersion was improved significantly.

COMPARATIVE EXAMPLE 4

The steps in example 2 were repeated expect that the fluorine-containing polymer 1 as a fluorine carbon surfactant was not added. The evaluating results for the pigment dispersion in comparative example 4 were shown in Table 6.

TABLE 6

The changes of particle diameter and viscosity of pigment particles in the pigment dispersion of comparative example 4 with the lapse of time

| Time (day) | 1 | 2 | 3 | 7 | 30 | 60 | 90 |
|---|---|---|---|---|---|---|---|
| Particle diameter (nm) (25° C.) | 47.38 | 60.34 | 88.62 | 98.45 | 126.33 | 158.96 | 200.11 |
| Particle diameter (nm) (41° C.) | 47.55 | 59.33 | 83.67 | 95.69 | 108.98 | 160.33 | 202.35 |
| Viscosity (cps) (25° C.) | 4.51 | 7.86 | 17.49 | 31.25 | flocculation | flocculation | flocculation |
| Viscosity (cps) (41° C.) | 4.55 | 7.98 | 17.63 | 29.65 | flocculation | flocculation | flocculation |
| State of precipitation | No | A little sand like precipitate | A lot of sand like precipitate | A thick layer of precipitate on the bottom | A thick layer of precipitate on the bottom | A thick layer of precipitate on the bottom | A thick layer of precipitate on the bottom |

Figure 8:
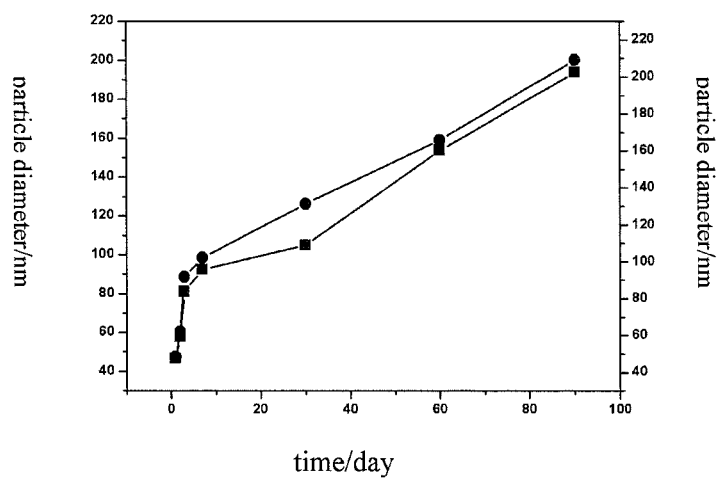
FIGS. 8-10 are charts showing the relation between the particle diameters of the pigments in the pigment dispersions of comparative examples 4-6 and the lapse of time, respectively.

The relation between the changes of the particle diameter of the pigment particles in the above pigment dispersion and the lapse of time was shown in FIG. 8. From the results in Table 6 and FIG. 8, it can be seen that when the surfactant was not added, the particle diameter in the pigment dispersion upon discharging could reach about 47 nm. However, after one day, the particle diameter increased quickly and reached near 100 nm in one week. The viscosity also increased continuously and after one week, viscosity of the pigment dispersion became about 30 cps. After one month, the pigment dispersion became a state of flocculation. The stability of the pigment dispersion was very poor.

COMPARATIVE EXAMPLE 5

The steps in example 2 were repeated expect that the fluorine-containing polymer 1 as a fluorine carbon surfactant was not added during the pre-dispersion stage, instead, it was added about one hour after the beginning of the grinding step. The evaluating results for the pigment dispersion in comparative example 5 were shown in Table 7.

TABLE 7

The changes of particle diameter and viscosity of pigment particles in the pigment dispersion of comparative example 5 with the lapse of time

| Time (day) | 1 | 2 | 3 | 7 | 30 | 60 | 90 |
|---|---|---|---|---|---|---|---|
| Particle diameter (nm) (25° C.) | 47.02 | 49.34 | 50.62 | 58.41 | 66.98 | 80.33 | 120.33 |
| Particle diameter (nm) (41° C.) | 47.04 | 50.56 | 52.33 | 59.69 | 65.28 | 79.69 | 123.37 |
| Viscosity (cps) (25° C.) | 4.51 | 4.84 | 15.36 | 25.43 | flocculation | flocculation | flocculation |
| Viscosity (cps) (41° C.) | 4.54 | 4.89 | 16.33 | 24.56 | flocculation | flocculation | flocculation |
| State of precipitation | No | No | No | No | A little precipitate | A little precipitate | A little precipitate |

Figure 9:
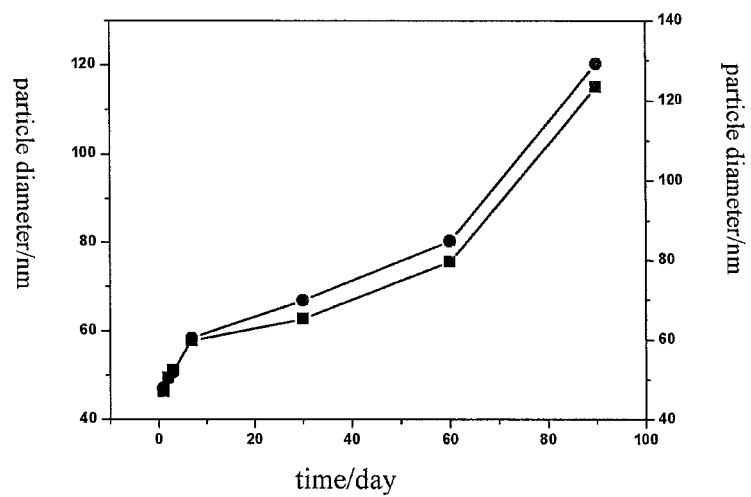

The relation between the changes of the particle diameter of the pigment particles in the above pigment dispersion and the lapse of time was shown in FIG. 9. From the results in Table 7 and FIG. 9, it can be seen that when the surfactant was added during the grinding stage, the change degree of the pigment particle diameter and viscosity with the lapse of time in one week became smaller, which was better than the case in comparative example 4 where the surfactant was not added. But the change of viscosity was relatively large, and increased continuously and more quickly with the lapse of time. There was no precipitate occurred on the bottom of the container in one week, but a little sand like precipitate occurred on the bottom of the container after one week. Thus, it can be seen that the stability of the pigment dispersion was inferior.

COMPARATIVE EXAMPLE 6

The steps in example 2 were repeated expect that the fluorine-containing polymer 1 as a fluorine carbon surfactant was not added during the pre-dispersion stage and the grinding stage, instead, the fluorine-containing polymer 1 was added alone after the grinding stage, and then the mixture was stirred at a rotating rate of about 500 rpm for about 10 min to mix it uniformly. The evaluating results for the pigment dispersion in comparative example 6 were shown in Table 8.

TABLE 8

The changes of particle diameter and viscosity of pigment particles in the pigment dispersion of comparative example 6 with the lapse of time

| Time (day) | 1 | 2 | 3 | 7 | 30 | 60 | 90 |
|---|---|---|---|---|---|---|---|
| Particle diameter (nm) (25° C.) | 47.25 | 48.56 | 54.96 | 58.33 | 68.25 | 99.88 | 152.33 |
| Particle diameter (nm) (41° C.) | 47.88 | 49.01 | 53.23 | 58.69 | 65.65 | 95.25 | 145.69 |
| Viscosity (cps) (25° C.) | 4.52 | 4.69 | 4.96 | 5.33 | 15.69 | 25.57 | flocculation |
| Viscosity (cps) (41° C.) | 4.54 | 4.68 | 4.89 | 5.23 | 16.02 | 24.69 | flocculation |
| State of precipitation | No | No | No | No | A little precipitate | A little precipitate | A little precipitate |

Figure 10:
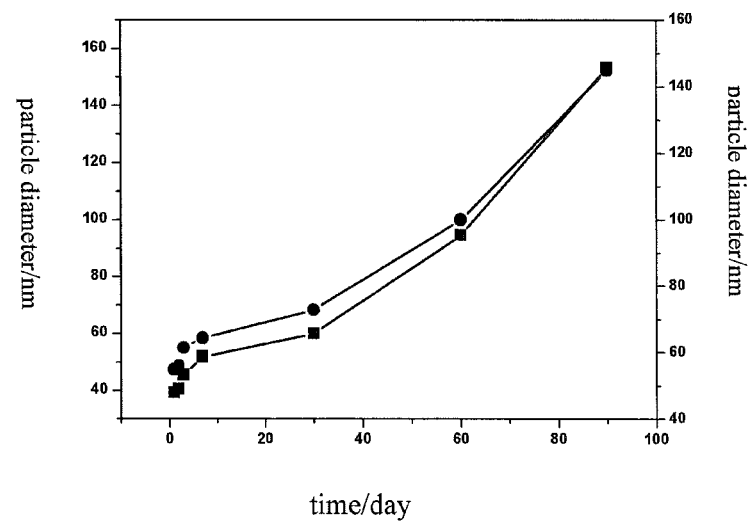

The relation between the change of particle diameter of pigment particles in the above pigment dispersion and the lapse of time was shown in FIG. 10. From the results in Table 8 and FIG. 10, it can be seen that when the surfactant was added after the grinding stage, the change degree of the pigment particle diameter and viscosity with the lapse of time in one week became smaller, which was better than comparative example 4 where the surfactant was not added. However, the pigment particle diameter and viscosity still increased continuously and more quickly with the lapse of time. In one week, a little precipitate occurred on the bottom of the container, and it increased continuously, but the amount of the precipitate was obviously less than that in comparative example 4. Thus, it can be seen that the stability of the pigment dispersion was still inferior.

From the results in example 2 and comparative examples 4-6, it can be seen that when a certain amount of the fluorine-containing polymer according to the invention was added as a fluorine carbon surfactant during the pre-dispersion stage, the changes of the particle diameter and viscosity of the pigment particles in the obtained pigment dispersion with the lapse of time would become very small and there was no precipitate produced. Thus, the stability of the pigment dispersion was improved significantly.

EXAMPLE 3

Pigment Dispersion Comprising Fluorine-Containing Polymer 2

Into a clean feed cylinder, 3 parts by weight of ethyl 3-ethoxylpropionate solvent was added, and then 0.5 part by weight of solsperse 32000 dispersant, 0.15 part by weight of A81 resin, 0.05 part by weight of solsperse 22000 pigment intensifier were add into the feed cylinder in turn. The mixture was stirred under a rotating rate of 3000 rpm for about 40 min. Then, the obtained mixture was added with 1 part by weight of G58 pigment and 0.08 part by weight of fluorine-containing polymer 2, and stirred under a rotating rate of 3000 rpm for about 30 min to obtain a pigment mixture.

(2) Grinding

The process in the grinding was the same as that in example 1.

The evaluating results (according to the same method as mentioned in example 1) for the pigment dispersion in example 3 were shown in Table 9.

TABLE 9

The changes of particle diameter and viscosity of pigment particles in the pigment dispersion of example 3 with the lapse of time

| Time (day) | 1 | 2 | 3 | 7 | 30 | 60 | 90 |
|---|---|---|---|---|---|---|---|
| Particle diameter (nm) (25° C.) | 47.33 | 48.32 | 48.59 | 48.63 | 47.39 | 48.20 | 48.64 |
| Particle diameter (nm) (41° C.) | 48.68 | 47.34 | 48.98 | 48.65 | 47.05 | 47.79 | 48.06 |
| Viscosity (cps) (25° C.) | 4.49 | 4.53 | 4.52 | 4.58 | 4.55 | 4.51 | 4.58 |
| Viscosity (cps) (41° C.) | 4.47 | 4.56 | 4.54 | 4.46 | 4.47 | 4.53 | 4.51 |
| State of precipitation | No | No | No | No | No | No | No |

Figure 11:
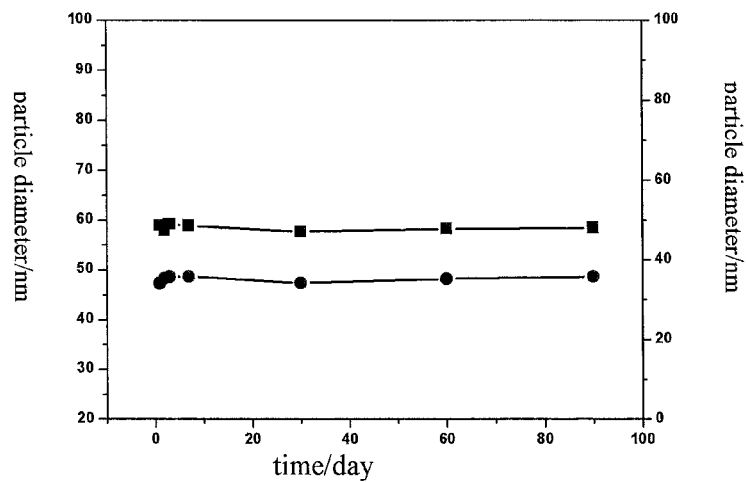
FIG. 11 is a chart showing the relation between the particle diameter of the pigment in the pigment dispersion of example 3 and the lapse of time.
Figure 12:
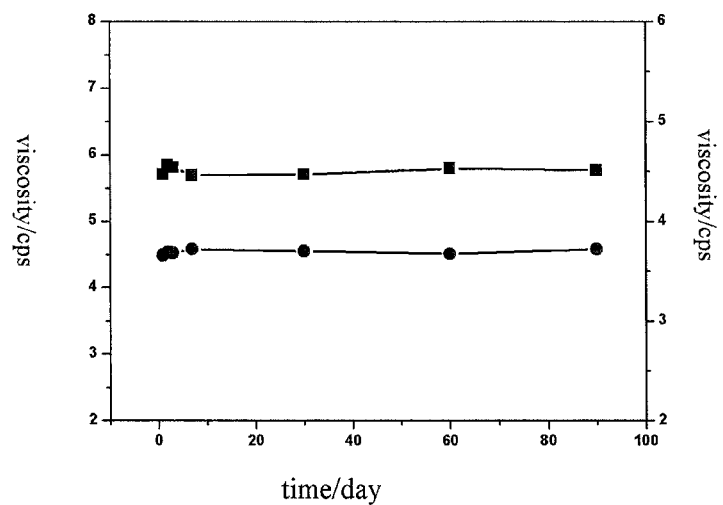
FIG. 12 is a chart showing the relation between the viscosity of the pigment in the pigment dispersion of example 3 and the lapse of time.

The relation between the changes of the viscosity and particle diameter of the pigment particles in the above pigment dispersion and the lapse of time were shown in FIGS. 11 and 12. From the results in Table 9 and FIGS. 11 and 12, it can be seen that when the fluorine-containing polymer 2 as a fluorine carbon surfactant was added during the pre-dispersion stage, the changes of the viscosity and particle diameter of the obtained pigment particles were all very small, and there was no precipitate produced, and thus, the stability of the pigment dispersion was improved significantly.

COMPARATIVE EXAMPLE 7

The steps in example 3 were repeated expect that the fluorine-containing polymer 2 as a fluorine carbon surfactant was not added. The evaluating results for the pigment dispersion obtained in comparative example 7 were shown in Table 10.

TABLE 10

The changes of particle diameter and viscosity of pigment particles in the pigment dispersion of comparative example 7 with the lapse of time

| Time (day) | 1 | 2 | 3 | 7 | 30 | 60 | 90 |
|---|---|---|---|---|---|---|---|
| Particle diameter (nm) (25° C.) | 48.65 | 58.36 | 67.55 | 81.23 | 109.69 | 142.32 | 198.61 |
| Particle diameter (nm) (41° C.) | 47.68 | 61.58 | 71.89 | 82.32 | 107.97 | 142.35 | 200.12 |
| Viscosity (cps) (25° C.) | 4.53 | 7.56 | 18.89 | 30.25 | flocculation | flocculation | flocculation |
| Viscosity (cps) (41° C.) | 4.58 | 7.23 | 16.57 | 28.98 | flocculation | flocculation | flocculation |
| State of precipitation | No | A little sand like precipitate | A lot of sand like precipitate | A thick layer of precipitate on the bottom | A thick layer of precipitate on the bottom | A thick layer of precipitate on the bottom | A thick layer of precipitate on the bottom |

Figure 13:
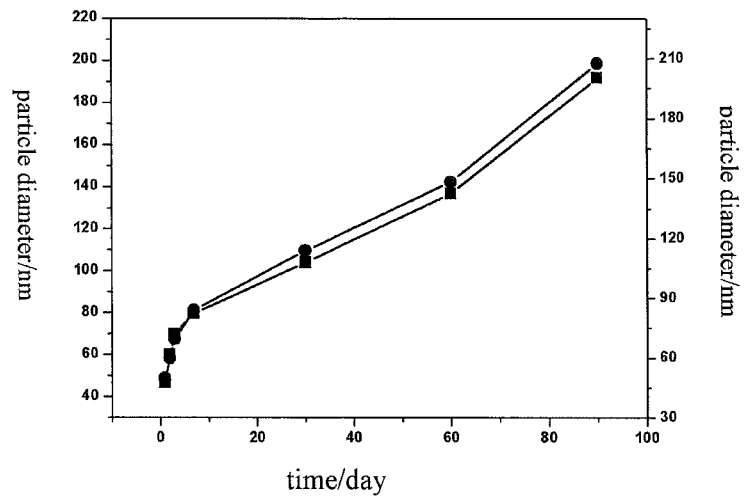
FIGS. 13-15 are charts showing the relation between the particle diameters of the pigments in the pigment dispersions of comparative examples 7-9 and the lapse of time, respectively.

The relation between the changes of the particle diameter of the pigment particles in the above pigment dispersion and the lapse of time was shown in FIG. 13. From the results in Table 10 and FIG. 13, it can be seen that when the surfactant was not added, the particle diameter in the pigment dispersion upon discharging could reach about 47 nm. However, after one day, the particle diameter increased quickly and reached near 80 nm in one week. The viscosity also increased continuously and after one week, viscosity of the pigment dispersion became about 30 cps. After one month, the pigment dispersion became a state of flocculation. The stability of the pigment dispersion was very poor.

COMPARATIVE EXAMPLE 8

The steps in example 3 were repeated expect that the fluorine-containing polymer 2 as a fluorine carbon surfactant was not added during the pre-dispersion stage, instead, it was added about one hour after the beginning of the grinding step. The evaluating results for the pigment dispersion obtained in comparative example 8 were shown in Table 11.

TABLE 11

The changes of particle diameter and viscosity of pigment particles in the pigment dispersion of comparative example 8 with the lapse of time

| Time (day) | 1 | 2 | 3 | 7 | 30 | 60 | 90 |
|---|---|---|---|---|---|---|---|
| Particle diameter (nm) (25° C.) | 47.53 | 51.25 | 55.69 | 62.56 | 68.79 | 78.66 | 110.23 |
| Particle diameter (nm) (41° C.) | 47.38 | 50.27 | 56.22 | 60.32 | 67.65 | 80.22 | 115.36 |
| Viscosity (cps) (25° C.) | 4.55 | 4.91 | 15.33 | 26.12 | flocculation | flocculation | flocculation |
| Viscosity (cps) (41° C.) | 4.54 | 4.93 | 15.65 | 25.63 | flocculation | flocculation | flocculation |
| State of precipitation | No | No | No | No | A little precipitate | A little precipitate | A little precipitate |

Figure 14:
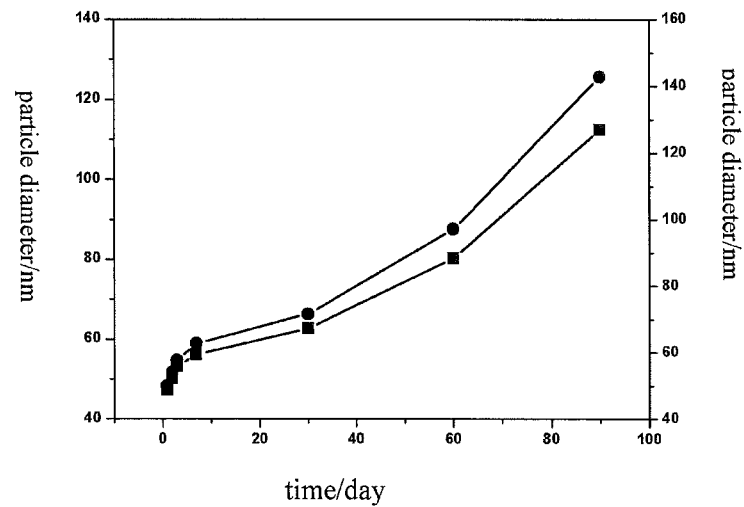

The relation between the changes of the particle diameter of the pigment particles in the above pigment dispersion and the lapse of time was shown in FIG. 14. From the results in Table 11 and FIG. 14, it can be seen that when the surfactant was added during the grinding stage, the change degree of the pigment particle diameter and viscosity with the lapse of time in one week became smaller, which was better than comparative example 7 where the surfactant was not added. But the change of viscosity was relatively large, and increased continuously and more quickly with the lapse of time. There was no precipitate occurred on the bottom of the container in one week, but a little sand like precipitate occurred on the bottom of the container after one week. Thus, it can be seen that the stability of the pigment dispersion was inferior.

COMPARATIVE EXAMPLE 9

The steps in example 3 were repeated expect that the fluorine-containing polymer 2 as a fluorine carbon surfactant was not added during the pre-dispersion stage and the grinding stage, instead, the fluorine-containing polymer 2 was added alone after the grinding stage, and then the mixture was stirred at a rotating rate of about 500 rpm for about 10 min to mix it uniformly. The evaluating results for the pigment dispersion in comparative example 9 were shown in Table 12.

TABLE 12

The changes of particle diameter and viscosity of pigment particles in the pigment dispersion of comparative example 9 with the lapse of time

| Time (day) | 1 | 2 | 3 | 7 | 30 | 60 | 90 |
|---|---|---|---|---|---|---|---|
| Particle diameter (nm) (25° C.) | 48.01 | 49.56 | 55.69 | 59.37 | 67.89 | 89.91 | 132.65 |
| Particle diameter (nm) (41° C.) | 47.98 | 50.02 | 56.36 | 60.25 | 66.58 | 91.26 | 130.46 |
| Viscosity (cps) (25° C.) | 4.48 | 4.81 | 4.97 | 5.42 | 14.36 | 24.56 | flocculation |
| Viscosity (cps) (41° C.) | 4.52 | 4.79 | 4.96 | 5.39 | 15.08 | 23.96 | flocculation |
| State of precipitation | No | No | No | No | A little precipitate | A little precipitate | A little precipitate |

Figure 15:
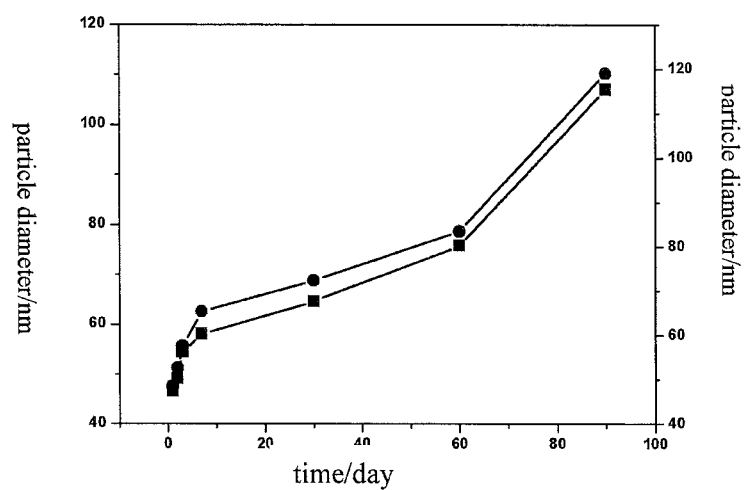

The relation between the change of the particle diameter of the pigment particles in the above pigment dispersion and the lapse of time was shown in FIG. 15. From the results in Table 12 and FIG. 15, it can be seen that when the surfactant was added after the grinding stage, the change degree of the pigment particle diameter and viscosity with the lapse of time in one week became smaller, which was better than comparative example 7 where the surfactant was not added. However, the changes still increased continuously and more quickly with the lapse of time. In one week, a little precipitate occurred on the bottom of the container, and it increased continuously, but the amount of the precipitate was obviously less than that in comparative example 7. Thus, it can be seen that the stability of the pigment dispersion was still inferior.

From the results in example 3 and comparative examples 7-9, it can be seen that when a certain amount of the fluorine-containing polymer according to the invention was added as a fluorine carbon surfactant during the pre-dispersion stage, the changes of the particle diameter and viscosity of the pigment particles in the obtained pigment dispersion with the lapse of time would become very small and there was no precipitate produced. Thus, the stability of the pigment dispersion was improved significantly.

EXAMPLE 4

Pigment Dispersion Comprising Fluorine-Containing Polymer 3

Into a clean feed cylinder, 5 parts by weight of propylene glycol methyl ether acetate solvent was added, and then 0.3 part by weight of BYK 21116 dispersant, 0.2 part by weight of A81 resin, 0.05 part by weight of BYK 2100 pigment intensifier were add into the feed cylinder in turn. The mixture was stirred under a rotating rate of 3000 rpm for about 40 min. Then, the obtained mixture was added with 1 part by weight of G58 pigment and 0.10 part by weight of fluorine-containing polymer 3, and stirred under a rotating rate of 3000 rpm for about 30 min to obtain a pigment mixture.

(2) Grinding

The process in the grinding was the same as that in example 1.

The evaluating results (according to the same method as mentioned in example 1) for the pigment dispersion in example 4 were shown in Table 13.

TABLE 13

The changes of particle diameter and viscosity of pigment particles in the pigment dispersion of example 4 with the lapse of time

| Time (day) | 1 | 2 | 3 | 7 | 30 | 60 | 90 |
|---|---|---|---|---|---|---|---|
| Particle diameter (nm) (25° C.) | 48.33 | 48.64 | 47.58 | 47.46 | 47.95 | 48.32 | 48.56 |
| Particle diameter (nm) (41° C.) | 48.12 | 48.39 | 47.98 | 47.65 | 47.55 | 48.94 | 48.66 |
| Viscosity (cps) (25° C.) | 4.58 | 4.51 | 4.55 | 4.48 | 4.52 | 4.51 | 4.54 |
| Viscosity (cps) (41° C.) | 4.46 | 4.54 | 4.49 | 4.47 | 4.53 | 4.53 | 4.49 |
| State of precipitation | No | No | No | No | No | No | No |

Figure 16:
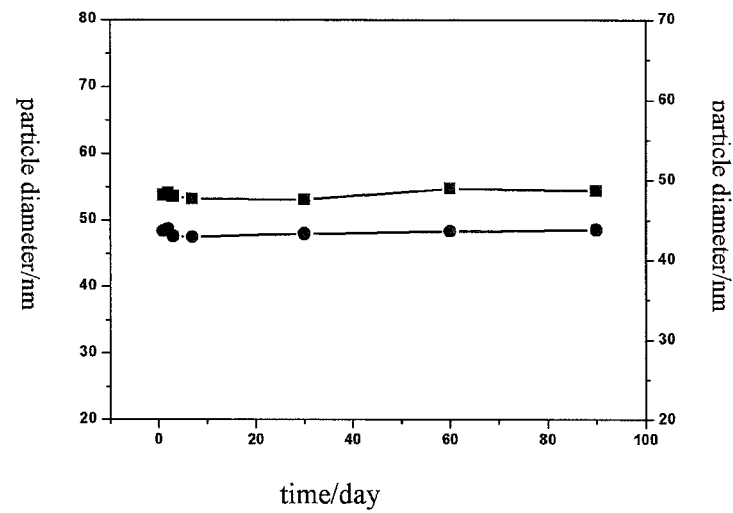
FIG. 16 is a chart showing the relation between the particle diameter of the pigment in the pigment dispersion of example 4 and the lapse of time.
Figure 17:
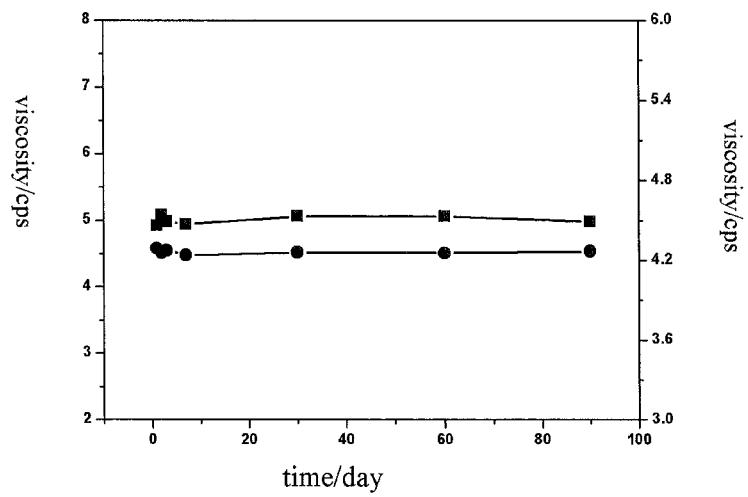
FIG. 17 is a chart showing the relation between the viscosity of the pigment in the pigment dispersion of example 4 and the lapse of time.

The relation between the changes of the viscosity and particle diameter of the pigment particles in the above pigment dispersion and the lapse of time were shown in FIGS. 16 and 17. From the results in Table 13 and FIGS. 16 and 17, it can be seen that when fluorine-containing polymer 3 as a fluorine carbon surfactant was added during the pre-dispersion stage, the changes of the viscosity and particle diameter of the obtained pigment particles were all very small, and there was no precipitate produced, and thus, the stability of the pigment dispersion was improved significantly.

COMPARATIVE EXAMPLE 10

The steps in example 4 were repeated expect that the fluorine-containing polymer 3 as a fluorine carbon surfactant was not added. The evaluating results for the pigment dispersion obtained in comparative example 10 were shown in Table 14.

TABLE 14

The changes of particle diameter and viscosity of pigment particles in the pigment dispersion of comparative example 10 with the lapse of time

| Time (day) | 1 | 2 | 3 | 7 | 30 | 60 | 90 |
|---|---|---|---|---|---|---|---|
| Particle diameter (nm) (25° C.) | 47.95 | 54.64 | 65.56 | 79.33 | 109.68 | 138.22 | 196.36 |
| Particle diameter (nm) (41° C.) | 47.85 | 55.32 | 67.38 | 81.25 | 110.59 | 141.98 | 198.65 |
| Viscosity (cps) (25° C.) | 4.55 | 8.21 | 20.32 | 31.64 | flocculation | flocculation | flocculation |
| Viscosity (cps) (41° C.) | 4.51 | 8.33 | 21.35 | 30.58 | flocculation | flocculation | flocculation |
| State of precipitation | No | A little sand like precipitate | A lot of sand like precipitate | A thick layer of precipitate on the bottom | A thick layer of precipitate on the bottom | A thick layer of precipitate on the bottom | A thick layer of precipitate on the bottom |

Figure 18:
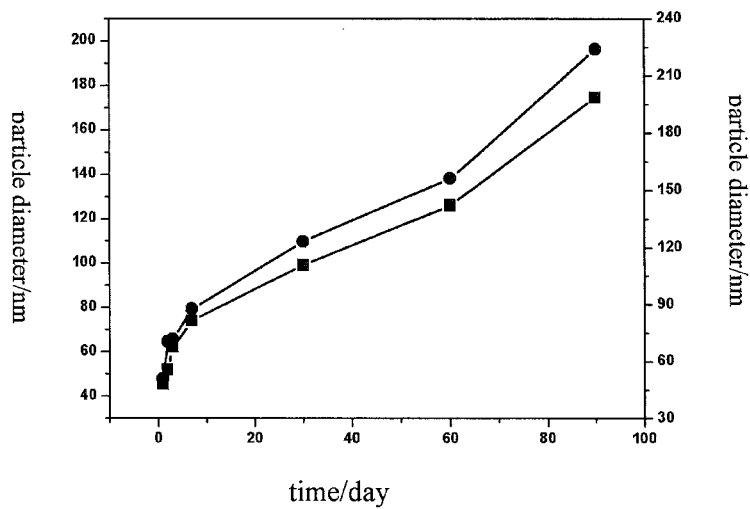
FIGS. 18-20 are charts showing the relation between the particle diameters of the pigments in the pigment dispersions of comparative examples 10-12 and the lapse of time, respectively.

The relation between the change of the particle diameter of the pigment particles in the above pigment dispersion and the lapse of time was shown in FIG. 18. From the results in Table 10 and FIG. 18, it can be seen that when the surfactant was not added, the particle diameter in the pigment dispersion upon discharging could reach about 47 nm. However, after one day, the particle diameter increased quickly and reached near 80 nm in one week. The viscosity also increased continuously and after one week, viscosity of the pigment dispersion became about 30 cps. After one month, the pigment dispersion became a state of flocculation. The stability of the pigment dispersion was very poor.

COMPARATIVE EXAMPLE 11

The steps in example 4 were repeated expect that the fluorine-containing polymer 3 as a fluorine carbon surfactant was not added during the pre-dispersion stage, instead, it was added about one hour after the beginning of the grinding step. The evaluating results for the pigment dispersion obtained in comparative example 11 were shown in Table 15.

TABLE 15

The changes of particle diameter and viscosity of pigment particles in the pigment dispersion of comparative example 11 with the lapse of time

| Time (day) | 1 | 2 | 3 | 7 | 30 | 60 | 90 |
|---|---|---|---|---|---|---|---|
| Particle diameter (nm) (25° C.) | 48.62 | 53.26 | 59.33 | 65.68 | 70.79 | 79.11 | 99.23 |
| Particle diameter (nm) (41° C.) | 48.32 | 52.98 | 58.79 | 64.36 | 69.52 | 80.35 | 98.97 |
| Viscosity (cps) (25° C.) | 4.49 | 7.85 | 18.69 | 28.31 | flocculation | flocculation | flocculation |
| Viscosity (cps) (41° C.) | 4.55 | 7.69 | 16.98 | 27.12 | flocculation | flocculation | flocculation |
| State of precipitation | No | No | No | No | A little precipitate | A little precipitate | A little precipitate |

Figure 19:
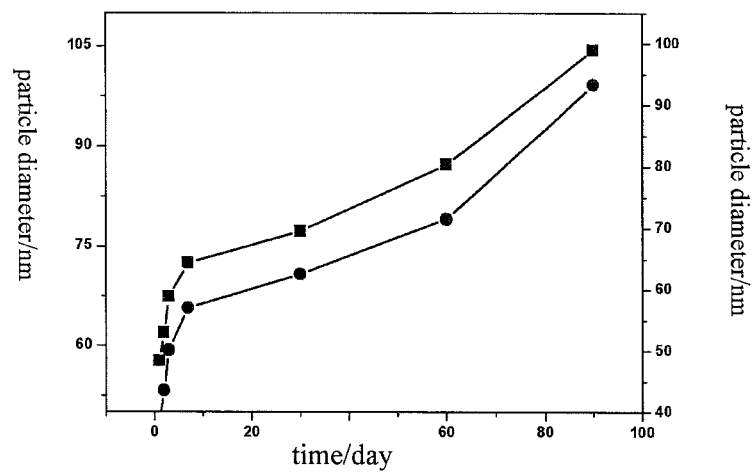

The relation between the change of the particle diameter of the pigment particles in the above pigment dispersion and the lapse of time was shown in FIG. 19. From the results in Table 15 and FIG. 19, it can be seen that when the surfactant was added during the grinding stage, the change degree of the pigment particle diameter and viscosity with the lapse of time in one week became smaller, which was better than comparative example 10 where the surfactant was not added. But the change of viscosity was relatively large, and increased continuously and more quickly with the lapse of time. There was no precipitate occurred on the bottom of the container in one week, but a little sand like precipitate occurred on the bottom of the container after one week. Thus, it can be seen that the stability of the pigment dispersion was inferior.

COMPARATIVE EXAMPLE 12

The steps in example 4 were repeated expect that the fluorine-containing polymer 3 as a fluorine carbon surfactant was not added during the pre-dispersion stage and the grinding stage, instead, the fluorine-containing polymer 3 was added alone after the grinding stage, and then the mixture was stirred at a rotating rate of about 500 rpm for about 10 min to mix it uniformly. The evaluating results for the pigment dispersion obtained in comparative example 12 were shown in Table 16.

TABLE 16

The changes of particle diameter and viscosity of pigment particles in the pigment dispersion of comparative example 12 with the lapse of time

| Time (day) | 1 | 2 | 3 | 7 | 30 | 60 | 90 |
|---|---|---|---|---|---|---|---|
| Particle diameter (nm) (25° C.) | 48.33 | 51.65 | 54.76 | 58.96 | 66.35 | 87.58 | 125.68 |
| Particle diameter (nm) (41° C.) | 48.65 | 52.14 | 55.86 | 59.37 | 67.22 | 88.34 | 126.92 |
| Viscosity (cps) (25° C.) | 4.46 | 4.77 | 5.02 | 6.37 | 12.33 | 22.73 | flocculation |
| Viscosity (cps) (41° C.) | 4.50 | 4.82 | 4.98 | 6.43 | 13.84 | 22.98 | flocculation |
| State of precipitation | No | No | No | No | A little precipitate | A little precipitate | A little precipitate |

Figure 20:
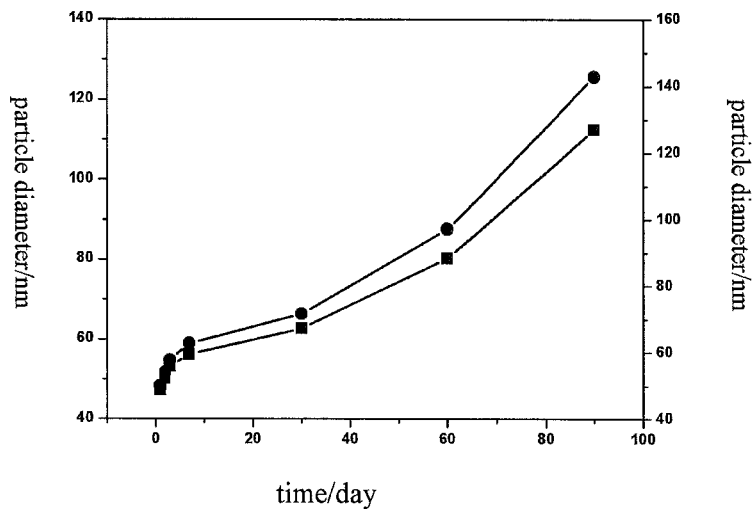

The relation between the change of the particle diameter of the pigment particles in the above pigment dispersion and the lapse of time was shown in FIG. 20. From the results in Table 16 and FIG. 20, it can be seen that when the surfactant was added after the grinding stage, the change degree of the pigment particle diameter and viscosity with the lapse of time in one week became smaller, which was better than comparative example 10 where the surfactant was not added. However, the changes still increased continuously and more quickly with the lapse of time. In one week, a little precipitate occurred on the bottom of the container, and it increased continuously, but the amount of the precipitate was obviously less than that in comparative example 10. Thus, it can be seen that the stability of the pigment dispersion was still inferior.

From the results in example 4 and comparative examples 11-12, it can be seen that when a certain amount of the fluorine-containing polymer according to the invention was added as a fluorine carbon surfactant during the pre-dispersion stage, the changes of the particle diameter and viscosity of the pigment particles in the obtained pigment dispersion with the lapse of time would become very small and there was no precipitate produced. Thus, the stability of the pigment dispersion was improved significantly.

From the results in example 1 and examples 2-4, it can be seen that the particle diameters of the pigment particles obtained examples 2-4 are relative smaller, and the viscosities thereof are also lower, and thus, the stabilization effect of the fluorine carbon surfactants prepared in examples 2-4 are better than that of the existing fluorine carbon surfactant.

Although the invention has been described in detail above by general description and specific embodiments, they can be modified or improved based on the invention, which is obvious for those skilled in the art. Thus, these modification and improvement made without departing from the spirit of the invention all fall into the protection scope of the invention.

What is claimed is:

1. A fluorine-containing polymer comprising a structure represented by a general formula (I):

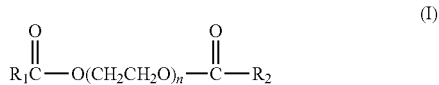

wherein, $R_1$ is a C1-C10 perfluoroalkyl group; $R_2$ is a substituted or unsubstituted group selected from a phenyl group, a benzyl group, a benzo-heterocyclic group or a naphthyl group; and
n=3-35.

2. The fluorine-containing polymer according to claim 1, wherein n=4-30.

3. The fluorine-containing polymer according to claim 1, wherein, in the substituted $R_2$ group, the substituent is a C1-C5 alkyl group, a C2-C5 alkenyl group, a C1-C5 alkoxy group, a C2-C5 acyl group, or a halogen atom.

4. The fluorine-containing polymer according to claim 1, wherein $R_1$ is a C1-C5 perfluoroalkyl group; and $R_2$ is a phenyl group, a benzodihydropyranyl group or a naphthyl group.

5. A process for preparing the fluorine-containing polymer according to claim 1, comprising the steps of:
   (1) preparing a perfluoroalkyl carboxylic acid having the following formula:
   $R_1COOH$,
   wherein $R_1$ is a C1-C10 perfluoroalkyl group;
   (2) subjecting the perfluoroalkyl carboxylic acid in step (1) and a polyethylene glycol to an esterification reaction to obtain a polyethylene glycol monoester product;
   (3) subjecting the esterification product obtained in step (2) and a carboxylic acid $R_2$—COOH to an esterification reaction to obtain the fluorine-containing polymer, wherein $R_2$ is a substituted or unsubstituted group selected from a phenyl group, a benzyl group, a benzo-heterocyclic group or a naphthyl group.

6. The process according to claim 5, wherein the perfluoroalkyl carboxylic acid is obtained from a perfluoroalkyl acyl halide as a starting material through esterification and hydrolysis.

7. The process according to claim 5, wherein the polyethylene glycol is $HO(CH_2CH_2O)_nH$, wherein n=3-35.

8. A pigment dispersion comprising a pigment, wherein the pigment dispersion further comprises a non-ionic fluorine carbon surfactant which is the fluorine-containing polymer according to claim 1.

9. The pigment dispersion according to claim 8, wherein the weight of the non-ionic fluorine carbon surfactant is 1-15% of the weight of the pigment.

10. The pigment dispersion according to claim 8, wherein the pigment dispersion comprises by weight the following ingredients of:

| | |
|---|---|
| pigment: | 1 part; |
| solvent: | 0.5-10 parts; |
| dispersant: | 0.05-1.0 parts; |
| resin: | 0.01-1.0 parts; |
| pigment intensifier: | 0.01-0.5 parts; |
| non-ionic fluorine carbon surfactant: | 0.01-0.15 parts. |

11. The pigment dispersion according to claim 10, wherein the pigment dispersion comprises by weight the following ingredients of:

| | |
|---|---|
| pigment: | 1 part; |
| solvent: | 1-5 parts; |
| dispersant: | 0.1-0.8 parts; |
| resin: | 0.05-0.5 parts; |
| pigment intensifier: | 0.01-0.1 parts; |
| non-ionic fluorine carbon surfactant: | 0.03-0.1 parts. |

12. The pigment dispersion according to claim 10, wherein the solvent is selected from propylene glycol methyl ether acetate, propylene glycol diacetate, or ethyl 3-ethoxylpropionate.

13. The pigment dispersion according to claim 10, wherein the dispersant is a solvent type wetting dispersant.

14. The pigment dispersion according to claim 10, wherein the resin is selected from an epoxy resin or a phenolic resin.

15. The pigment dispersion according to claim 10, wherein the pigment intensifier is selected from an azo type pigment intensifier, a phthalocyanin type pigment intensifier, or a quinacridone type pigment intensifier.

16. A process for preparing the pigment dispersion according to claim 10, comprising the steps of:
   (1) a pre-dispersing step wherein a pigment mixture is obtained by mixing and stirring a solvent, a dispersant, a resin and a pigment intensifier uniformly, adding a pigment and a non-ionic fluorine carbon surfactant, and then stirring uniformly;
   (2) a grinding step wherein the obtained pigment mixture is grained to obtain the pigment dispersion.

\* \* \* \* \*